United States Patent
Carey et al.

(10) Patent No.: US 6,180,071 B1
(45) Date of Patent: Jan. 30, 2001

(54) PROCESS FOR RECOVERING RHODIUM CATALYST

(75) Inventors: John Laurence Carey; Michael David Jones, both of East Yorkshire; Gillian Mary Lancaster, Brough, all of (GB)

(73) Assignee: BP Chemicals Limited, London (GB)

( * ) Notice: Under 35 U.S.C. 154(b), the term of this patent shall be extended for 0 days.

(21) Appl. No.: 09/274,997

(22) Filed: Mar. 24, 1999

(30) Foreign Application Priority Data

Mar. 26, 1998 (GB) .................................................. 9806527

(51) Int. Cl.⁷ ............................ C01G 55/00; C22B 11/00
(52) U.S. Cl. .......................................................... 423/22
(58) Field of Search ............................... 423/22; 502/22; 562/891, 898

(56) References Cited

U.S. PATENT DOCUMENTS

| | | | |
|---|---|---|---|
| 3,927,078 | 12/1975 | Lapporte et al. | 560/232 |
| 4,021,463 | 5/1977 | Kummer et al. | 556/16 |
| 4,046,807 | 9/1977 | Kuckertz | 562/891 |
| 4,340,569 | 7/1982 | Davidson et al. | 423/22 |
| 4,340,570 | 7/1982 | Davidson | 502/26 |
| 4,341,741 | 7/1982 | Davidson et al. | 423/22 |
| 4,364,907 | 12/1982 | Barnes | 423/22 |
| 4,374,070 | 2/1983 | Larkins et al. | 562/891 |
| 4,388,217 | 6/1983 | Hembre et al. | 502/28 |
| 4,390,473 | 6/1983 | Cooper | 556/136 |
| 4,396,551 | 8/1983 | Tsunoda et al. | 556/23 |
| 4,430,273 | 2/1984 | Erpenbach | 562/891 |
| 4,434,240 | 2/1984 | Pugach | 502/24 |
| 4,559,183 | 12/1985 | Hewlett | 562/891 |
| 4,650,649 | * 3/1987 | Zoeller | 423/22 |
| 4,795,538 | 1/1989 | Caude | 205/556 |
| 4,944,927 | 7/1990 | Gulliver | 358/426 |
| 4,945,075 | 7/1990 | Cushman et al. | 502/24 |
| 5,100,850 | 3/1992 | Fillers et al. | 502/24 |
| 5,364,822 | 11/1994 | Carey | 502/24 |

FOREIGN PATENT DOCUMENTS

| | | |
|---|---|---|
| 0008 396 | 3/1980 | (EP) . |
| 0087 870 | 9/1983 | (EP) . |
| 0 255 389 | 2/1988 | (EP) . |
| 0 618 009 A1 | 10/1994 | (EP) . |
| 82/01829 | 6/1982 | (WO) . |
| 91/07372 | 5/1991 | (WO) . |

* cited by examiner

Primary Examiner—Steven Bos
(74) Attorney, Agent, or Firm—Nixon & Vanderhye

(57) ABSTRACT

A process for recovery rhodium from a solution of rhodium and tar produced in the carbonylation of methanol, methyl acetate dimethyl ester and/or reactive derivatives thereof involves extraction with a combination of water, methyl iodide and methyl acetate in which methyl acetate is at least 20% of the methyl iodide plus methyl acetate.

38 Claims, 1 Drawing Sheet

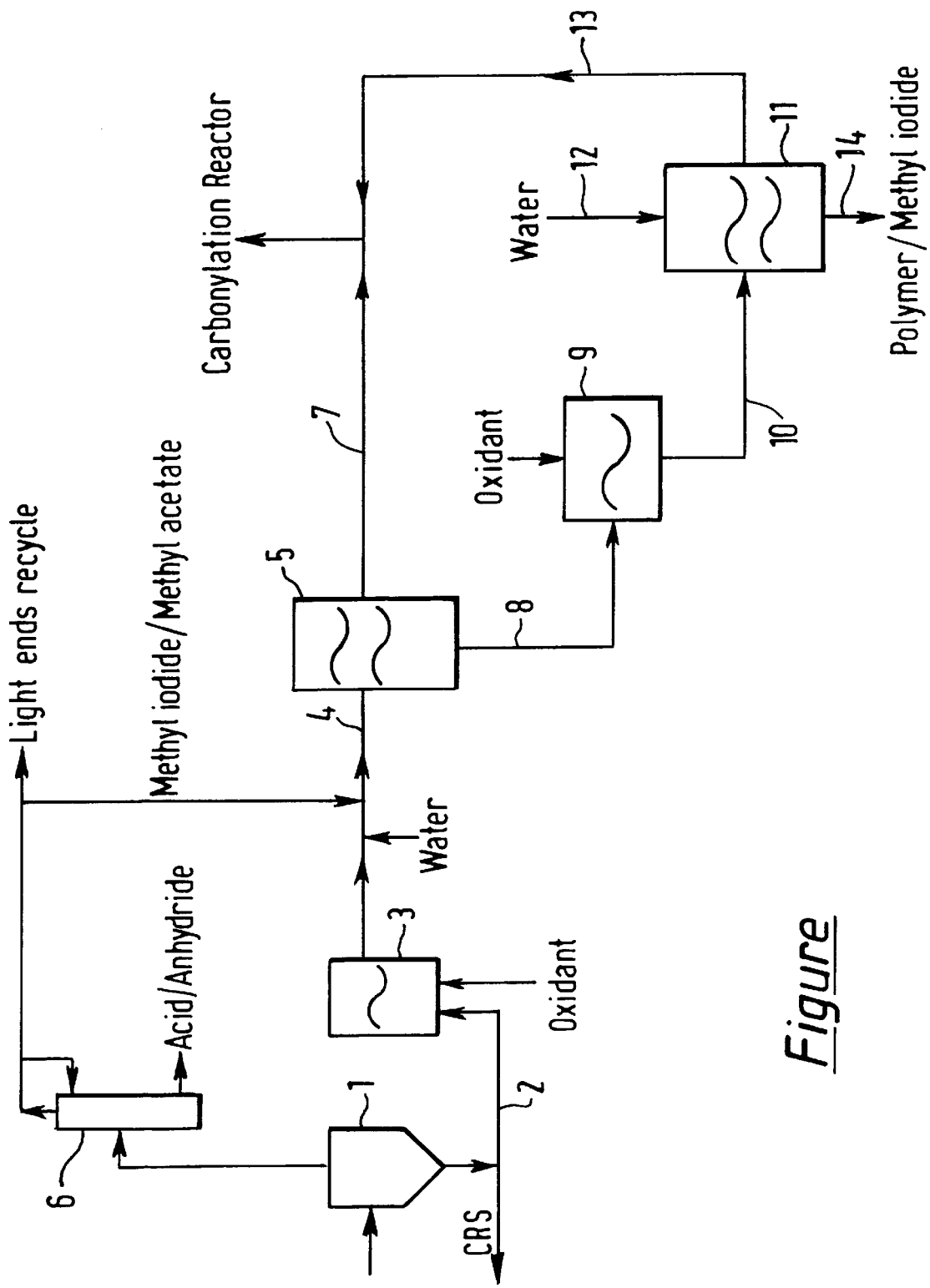
*Figure*

PROCESS FOR RECOVERING RHODIUM CATALYST

The present invention relates to a process for recovering rhodium catalyst from tar (or "polymer") formed during the preparation of acetic anhydride and/or acetic acid by the rhodium catalysed carbonylation of methyl acetate and/or dimethyl ether in the presence of methyl iodide as co-catalyst.

The use of catalyst systems comprising rhodium and an iodine compound in the preparation of acetic anhydride by the carbonylation of methyl acetate is well known from for example U.S. Pat. Nos. 3,927,078; 4,046,807; 4,374,070; and 4,559,183 and European Patents Publication Nos. 8396 and 87870. EP-A-87870, for example, discloses a process for the production of acetic anhydride with or without the net co-production of acetic acid from methanol and carbon monoxide in a series of esterification, carbonylation and separations steps comprising:

(1) reacting methanol with recycle acetic acid in an esterification step to form an esterification product containing predominantly methyl acetate, water and optionally unreacted methanol,
(2) removing part of the water from the esterification product,
(3) reacting the esterification product still containing water with carbon monoxide in a carbonylation step in the presence as catalyst of free or combined metallic carbonylation catalyst and as promoter of free or combined halogen to form a carbonylation product containing acetic acid and acetic anhydride,
(4) separating the carbonylation product by fractional distillation into a low boiling fraction containing carbonylation feed and volatile carbonylation promoter components, acetic acid and acetic anhydride fractions, and a higher boiling fraction containing carbonylation catalyst components,
(5) recycling the low boiling fraction containing carbonylation feed and carbonylation promoter components and the higher boiling fraction containing carbonylation catalyst components to the carbonylation step and,
(6) recycling at least part of the acetic acid fraction to the esterification step.

In practice, in step (4) of the aforesaid process, flash separation/distillation of a stream from the reactor removes methyl iodide, methyl acetate, acetic acid, acetic anhydride and other volatile components from a return stream containing the catalyst and promoter components, acetic acid, acetic anhydride and other relatively high boiling components. The overheads/volatile stream from the flash separation/distillation is fed to a fractional distillation where methyl iodide, methyl acetate and other light boiling components are separated from acetic acid, acetic anhydride and other heavy boiling components. The low boiling fraction from the distillation is then recycled to the reactor as described and the high boiling catalyst-containing fraction from the flash is recycled to the reactor.

A problem commonly encountered in the aforesaid processes for the production of acetic anhydride is the formation of tar (or "polymer"). The tar accumulates in those high-boiling fractions also containing carbonylation catalyst components. It is known from, for example, U.S. Pat. Nos. 4,388,217; 4,945,075; 4,944,927 and 5,364,822 to be removable therefrom by solvent extraction.

U.S. Pat. No. 4,388,217 relates to a process for the recovery of catalyst values from a catalyst-tar solution derived from a production system in which acetic anhydride is prepared by carbonylating methyl acetate in the presence of rhodium, lithium and methyl iodide wherein the catalyst-tar solution is submitted to an extraction using methyl iodide and aqueous hydrogen iodide and recovering catalyst values in the aqueous phase.

U.S. Pat. No. 4,945,075 relates to a process for the recovery of rhodium catalyst values from a catalyst-tar solution derived from a production system in which acetic anhydride is prepared by contacting a mixture of methyl acetate and/or dimethyl ether and methyl iodide with carbon monoxide in the presence of a rhodium catalyst comprising the steps of:

(1) submitting the catalyst-tar solution to an extraction with a combination of methyl iodide and aqueous hydrogen iodide and recovering (a) the aqueous phase containing most of the rhodium catalyst values, and (b) the methyl iodide phase containing most of the tar which contains minor amounts of the rhodium catalyst values;
(2) treating the methyl iodide phase of step (1) with an oxidant selected from peracetic acid, hydrogen peroxide and ozone; and
(3) submitting the treated methyl iodide phase of step (2) to an extraction with aqueous hydrogen iodide to recover in the aqueous phase rhodium catalyst values present in the treated methyl iodide phase.

The presence of aqueous hydrogen iodide in the aforesaid process is said to be necessary to stabilise the water-soluble rhodium compound or compounds, thereby preventing the loss of insoluble rhodium which can plate out on the extraction equipment and/or the walls of pipes, vessels, etc. A disadvantage of using hydrogen iodide is that at high concentrations it can result in corrosion of metal plant. Moreover, it is not generally employed in carbonylation processes for the production of acetic anhydride.

In the commercial operation of the process described in EP-A-87870, for example, polymer is continuously removed from the reactor by taking a small bleed from the catalyst recycle stream (CRS).

U.S. Pat. No. 4,944,927 describes a process in which tar, for example in CRS, undergoes an initial wash/contact with methyl iodide and optionally water after which the resulting rhodium/tar/methyl iodide rich phase is fed into an extraction column (e.g. a Kuhni column) in which it is countercurrently extracted using acetic acid/water extractant. Recovered from the extraction column is the majority of the rhodium and any co-promoters. The methyl iodide employed for this purpose may be at least in part methyl iodide recovered from the extraction tar/methyl iodide process stream.

U.S. Pat. No. 5,364,822 describes a carbonylation catalyst recovery system as described in U.S. Pat. No. 4,944,927 in which the carboxylic acid/water extracting solution also comprises (iii) iodide salt co-promoter derived from the carbonylation process and (iv) alkyl halide. According to U.S. Pat. No. 5,364,822 the iodide salt co-promoter may be derived from the carbonylation process in a pre-extraction step. Thus by reference to FIG. 1 therein U.S. Pat. No. 5,364,822 describes a process in which a catalyst recycle stream (CRS) being a side stream of liquid phase from a carbonylation product recovery flash stage from a rhodium-catalysed carbonylation process for the co-production of acetic acid and acetic anhydride and comprising rhodium catalyst, methyl iodide carbonylation promoter, iodide salt of a quaternary amine carbonylation co-promoter (such as N,N'-dimethyl imidazolium iodide and its alkylated derivatives), tar and carbonylation reaction products is withdrawn from the carbonylation process, diluted with methyl iodide (MeI) and fed into static mixers (1). Water is also fed into the mixers. In the mixers the water, CRS and MeI are mixed and pass through cooler (10) and chiller (11) into setting vessel (2) where they are separated to produce a pre-extraction aqueous phase (12) and a pre-extraction methyl iodide phase (13). Prior to the coolers, in the pre-extraction mixers acetic anhydride is hydrolysed to acetic acid. The pre-extraction aqueous phase is saturated with methyl iodide. The pre-extraction methyl iodide phase comprising tar and Group VIII noble metal catalyst is fed alone line (3) to the top of a multistage extraction Kuhni column (4). The pre-extraction aqueous phase comprising acetic acid, water, methyl iodide and iodide salt of quaternary amine co-promoter has its methyl iodide and acetic acid concentrations adjusted to ensure that it is saturated with methyl iodide by addition of methyl iodide and acetic acid in line (5) and is then fed as extracting solution to the bottom of the Kuhni column (4). In the Kuhni column the methyl iodide-containing composition from the pre-extraction and aqueous extracting solution are contacted to produce an aqueous phase comprising Group VIII noble metal and iodide salt of quaternary amine co-promoter and a methyl iodide phase comprising tar. The aqueous phase is removed from the top of the Kuhni column through line (6) and recycled to the carbonylation process (not shown). The tar-containing methyl iodide phase is removed from the base of Kuhni column through line (7). The methyl iodide is separated from the tar in the methyl iodide phase, for example in an evaporator (not shown); the tar being disposed of e.g. by burning and the methyl iodide being recycled to mix with incoming tar-containing process stream in the process of the present invention and/or to the carbonylation process.

In addition to methyl iodide recovered from the tar/methyl iodide phase from the extraction in the processes described in U.S. Pat. Nos. 4,944,927 and 5,364,822 methyl iodide has also been recovered for use by distillation from the low boiling fraction containing carbonylation feed and volatile carbonylation promoter components, such as described in connection with step (4) of the process of EP-A-87870.

It has hitherto been thought necessary to use substantially pure methyl iodide for those purposes. Thus, U.S. Pat. No. 5,364,822 describes at col 8, line 41 the use of crude methyl iodide (99.4% methyl iodide 0.6% methyl acetate).

There remains therefore a need for an improved process for the recovery of rhodium from polymer-containing carbonylation products.

It has now been found that methyl iodide containing a significant amount of methyl acetate can be used in such processes.

Accordingly, the present invention provides a process for the recovery of rhodium from a solution comprising rhodium and polymer obtained from a process in which acetic anhydride and/or acetic acid is produced by carbonylating methanol, methyl acetate, dimethyl ether and/or reactive derivatives thereof which process comprises the steps of:

(a) submitting said solution to a liquid extraction with a combination of water, methyl iodide and methyl acetate in which combination methyl acetate is at least 20% by mass of the mass of methyl iodide plus methyl acetate, and (b) separating an aqueous phase containing rhodium from an organic phase comprising methyl acetate, methyl iodide, tar and any remaining rhodium.

An advantage of the recovery process of the present invention is that it employs methyl iodide and methyl acetate, both of which are desirable components of the carbonylation process.

The recovered aqueous phase containing rhodium is preferably recycled to the carbonylation process. If desired, water may be removed from the recovered aqueous phase before it is recycled to the carbonylation process.

Another advantage of the process of the present invention is that in the liquid extraction step (a), iodide ions, which can be present in the solution as a result of the use of iodide salt stabilizers, such as lithium iodide, can be efficiently removed in the separated aqueous phase. Typically, about 95% or more of the iodide ion can be removed in the aqueous phase and about 95% or more of the polymer can be removed in the organic phase.

The components of the combination of water, methyl iodide and methyl acetate may be added to the extraction separately or as mixtures.

In the liquid extraction process methyl iodide may suitably be from 20 to 80% by mass, typically from 40 to 60% by mass of the mass of methyl iodide plus methyl acetate. Water may be added in a ratio of (0.2 to 5):1 by mass relative to the mass of methyl acetate plus methyl iodide in the combination. Methyl acetate and methyl iodide in turn may be added to the CRS (bleed from the flash tank) in the mass ratio of methyl acetate plus methyl iodide:rhodium solution of (0.2 to 5):1.

Whilst methyl iodide and methyl acetate may be added to the extraction separately, a preferred source of a combination of methyl iodide and methyl acetate is the overhead fraction removed from a fractional distillation column separating with or without an intermediate flash distillation step a product formed by carbonylating methyl acetate in the presence of rhodium as catalyst and methyl iodide as co-catalyst into a low-boiling fraction comprising methyl iodide and methyl acetate and a higher-boiling fraction.

Preferably, a combination of methyl acetate and methyl iodide is obtained by continuously withdrawing liquid carbonylation reaction product comprising acetic anhydride and/or acetic acid, rhodium catalyst, methyl iodide co-catalyst, methyl acetate and polymer from a carbonylation reactor, passing the liquid carbonylation reaction product to a flash distillation zone from which there is removed an overhead fraction comprising acetic anhydride and/or acetic acid, methyl iodide and methyl acetate and there is removed from the base a fraction comprising acetic acid, acetic anhydride, rhodium catalyst and tar, feeding the overhead fraction from the flash distillation zone to an intermediate point in a flash distillation column from which there is recovered an overhead vapour fraction comprising methyl iodide and methyl acetate and from a point below the feed point a fraction comprising acetic anhydride and/or acetic acid. It is the overhead vapour fraction from the fractional distillation column which after condensing is preferably used without further separation at least in part as liquid extractant in the process of the present invention. Generally the fraction comprises an approximately equimass mixture of methyl iodide and methyl acetate. An advantage of using a mixture of methyl iodide and methyl acetate is that it avoids the necessity of separating methyl iodide from methyl acetate in a separate column, thereby economising on plant.

Methyl iodide and/or methyl acetate may also be added to the extraction, for example from subsequent recovery stages from tar.

The liquid carbonylation reaction product from which the combination of methyl acetate and methyl iodide is eventually recovered may be for example that obtained by operation of the process of EP-A-87870 as hereinbefore described. Alternatively it may be that of the process of our as yet unpublished UK application no. 9802027.4/EP application no. 99300359.9 (BP Case No. 8909) which discloses an anhydrous process for the production of acetic acid by the reaction of methanol and/or dimethyl ether with a gaseous reactant comprising carbon monoxide and hydrogen the hydrogen being present in an amount less than 9 mol %, in the presence of a catalyst system comprising at least one noble metal of Group VIII of the Periodic Table and specifically rhodium as catalyst and a halo-compound, specifically methyl iodide, as cocatalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm (v) sufficient iodide salt to provide from 0.5 to 20% by weight iodine as $I^-$ and (vi) acetic acid comprising the remainder of the composition.

Preferably, prior to step (a) of the process the solution comprising rhodium and tar is submitted to a treatment whereby the rhodium present therein is converted to a more easily extractable form. Suitably the treatment may be an oxidative treatment. This may take the form of heating the solution in the presence of an oxygen-containing gas, preferably air, suitably at a temperature in the range 60 to 80° C., for a time sufficient to convert the rhodium to a more extractable form. Alternatively, or in addition, the oxidative treatment may take the form of treatment with a carbonylation process compatible oxidant. Suitably such oxidants include hydrogen peroxide, ozone and peracetic acid, of which the preferred oxidant is peracetic acid. The amount of oxidant required is suitably such as to maximise the rhodium liberated from the tar and may readily be determined by one skilled in the art. The treatment may be accomplished at ambient temperature or elevated temperatures may be employed at normal pressures provided that these do not exceed 60–80° C. or that steps are taken to minimise/stop methyl iodide loss. Alternatively, higher temperatures may be used if superatmospheric pressures are employed. The treatment with oxidant may suitably be effected in a stirred reactor.

It is believed, though we do not wish to be bound by any theory, that the oxidative treatment converts rhodium initially in the form of difficulty extractable $[RhI_4(CO)_2]^-$ to rhodium in the form of more easily extractable $[RhI_5CO]^{2-}$.

The organic phase separated in step (b) of the process of the present invention comprising methyl acetate, methyl iodide and tar containing unextracted rhodium may thereafter be subjected to the following further steps:
(c) treatment with a carbonylation process compatible oxidant,
(d) submitting the product of step (c) to an extraction with water and
(e) recovering an aqueous phase containing rhodium and an organic phase comprising tar and methyl iodide.

In step (c) the organic phase from step (b) is treated with a carbonylation process compatible oxidant. This may be effected in a manner as hereinbefore described in connection with the oxidative treatment prior to step (a) of the process.

In step (d) the product of step (c) is submitted to an extraction with water and an aqueous phase containing rhodium and an organic phase comprising tar and methyl iodide is recovered (e). The aqueous phase is preferably recycled to the carbonylation process.

An embodiment of the process of the present invention will now be described with reference to the accompanying Figure which takes the form of a flow sheet. A continuous bleed is taken through line (2) from the catalyst recycle stream (CRS) removed from the base of a flash tank (1) in a process for the production of acetic anhydride and optionally also acetic acid by the process as described in EP-A-87870. The flash tank serves to effect a separation of liquid reaction composition comprising acetic anhydride, acetic acid, methyl acetate, rhodium catalyst, optional stabilizers, for example a quaternary ammonium salt and/or lithium iodide, methyl iodide co-catalyst and by-products including tar into a CRS comprising rhodium catalyst, any non-volatile promoter, any catalyst stabiliser, and polymer from the base and a lower-boiling fraction comprising acetic anhydride, acetic acid, methyl acetate and methyl iodide taken overhead. This lower-boiling fraction is thereafter separated in a fractional distillation column (6) into a light ends recycle stream comprising methyl iodide and methyl acetate, which is taken overhead and condensed, some of the condensate being returned to the column as reflux, and a fraction comprising acetic acid and acetic anhydride which is removed from the base of the column or as a side-draw below the feed point.

The bleed is subjected to an oxidative treatment in vessel (3) and fed through line (4) to a solvent extraction vessel (5). To the vessel (5) is also fed through line (4) a liquid comprising methyl iodide and methyl acetate, and water. The mixture comprising methyl iodide and methyl acetate is taken from the light ends recycle stream referred to hereinabove. From the solvent extraction vessel (5) is taken through line (7) an aqueous phase comprising dissolved rhodium which is returned to the carbonylation reactor (not shown). From the bottom of the extraction vessel is taken through line (8) a methyl iodide phase comprising dissolved tar and residual rhodium. This is fed to a stirred vessel (9) in which it is contacted with peracetic acid. From the vessel (9) it is then taken through line (10) to a vessel (11) in which it is contacted with water fed through line (12). Thereafter in vessel (11) an aqueous phase comprising dissolved rhodium is separated from a methyl iodide phase comprising dissolved tar. The aqueous phase is recycled to the carbonylation reactor through line (13) and the methyl iodide phase is removed through line (14). If desired, the tar may be recovered from the methyl iodide phase and the residual rhodium recovered therefrom in known manner, the methyl iodide being recycled for use in the extraction process and/or the carbonylation reactor.

The process of the present invention will now be illustrated with reference to the following Examples.

EXAMPLE 1

A sample of catalyst recycle stream (CRS) was contacted with water and simulated light ends recycle comprising methyl iodide and methyl acetate in the mass ratio 1:1.7:3.3. The resulting two phases were separated and efficiencies into the aqueous phase were recorded; the results observed were 9.5% rhodium efficiency and 95%+lithium efficiency. Only trace levels of tar were observed in the aqueous phase.

EXAMPLE 2

A sample of CRS was heated in air for 1 hour at 60° C. The treated sample was then contacted with light ends recycle and water in the ratio 1:1:2. The resulting two phases were separated and efficiencies into the aqueous phase were recorded; the results observed were 55% rhodium efficiency, 98% +lithium efficiency and 1% or less tar efficiency. This shows the benefit of preoxidation of the rhodium/tar solution.

We claim:

1. A process for the recovery of rhodium from a solution comprising rhodium and tar obtained from a process in which acetic anhydride and/or acetic acid is produced by carbonylating methanol, methyl acetate, dimethyl ether and/or reactive derivatives thereof which process comprises the steps of:
(a) submitting said solution to a liquid extraction with a combination of water, methyl iodide and methyl acetate in which combination methyl acetate is at least 20% by mass of the mass of methyl iodide plus methyl acetate, and
(b) separating an aqueous phase containing rhodium from an organic phase comprising methyl acetate, methyl iodide, tar and any remaining rhodium.

2. A process as claimed in claim 1 in which methyl iodide in said combination is from 20 to 80% by mass of the mass of methyl iodide plus methyl acetate.

3. A process as claimed in claim 2 in which methyl iodide in said combination is from 40 to 60% by mass of the mass of methyl iodide plus methyl acetate.

4. A process as claimed in claim 3 in which a combination of methyl acetate and methyl iodide is obtained by continuously withdrawing liquid carbonylation reaction product comprising acetic anhydride and/or acetic acid, rhodium catalyst, methyl iodide co-catalyst, methyl acetate and tar from a carbonylation reactor, passing the liquid carbonylation reaction product to a flash distillation zone from which there is removed an overhead fraction comprising acetic anhydride and/or acetic acid, methyl iodide and methyl acetate and there is removed from the base a fraction comprising acetic acid, acetic anhydride, rhodium catalyst and tar, and feeding the overhead fraction from the flash distillation zone to an intermediate point in a flash distillation column from which there is recovered an overhead vapour faction comprising methyl iodide and methyl acetate and from a point below the feed point a fraction comprising acetic anhydride and/or acetic acid, said overhead vapour fraction from said fractional distillation column being condensed and used without further separation at least in part, in step (a) as extractant.

5. A process as claimed in claim 1 in which water in said combination is in a ratio of (0.2 to 5):1 by mass relative to the mass of methyl acetate plus methyl iodide in said combination.

6. A process as claimed in claim 4 in which water in said combination is in a ratio of (0.2 to 5):1 by mass relative to the mass of methyl acetate plus methyl iodide in said combination.

7. A process as claimed in claim 1 in which in step (a) methyl iodide and methyl acetate are added to said rhodium solution in a mass ratio of methyl acetate plus methyl iodide:rhodium solution of (0.2 to 5):1.

8. A process as claimed in claim 5 in which in step (a) methyl iodide and methyl acetate are added to said rhodium solution in a mass ratio of methyl acetate plus methyl iodide:rhodium solution of (0.2 to 5):1.

9. A process as claimed in claim 6 in which in step (a) methyl iodide and methyl acetate are added to said rhodium solution in a mass ratio of methyl acetate plus methyl iodide:rhodium solution of (0.2 to 5):1.

10. A process as claimed in claim 1 in which prior to step (a) the solution comprising rhodium and tar is submitted to a treatment whereby the rhodium present therein is converted to a more easily extractable form.

11. A process as claimed in claim 10 in which said treatment is an oxidative treatment.

12. A process as claimed in claim 11 in which said oxidative treatment takes the form of heating the solution in the presence of an oxygen-containing gas.

13. A process as claimed in claim 12 in which said solution is heated at a temperature in the range 60 to 80° C. for a time sufficient to convert the rhodium to a more extractable form.

14. A process as claimed in claim 11 in which said oxidative treatment takes the form of treatment with a carbonylation process compatible oxidant.

15. A process as claimed in claim 14 in which said oxidant is selected from the group consisting of hydrogen peroxide, ozone and peracetic acid.

16. A process as claimed in claim 4 in which prior to step (a) the solution comprising rhodium and tar is submitted to a treatment whereby the rhodium presented therein is converted to a more easily extractable form.

17. A process as claimed in claim 16 in which said treatment is an oxidative treatment.

18. A process as claimed in claim 8 in which prior to step (a) the solution comprising rhodium and tar is submitted to a treatment whereby the rhodium presented therein is converted to a more easily extractable form.

19. A process as claimed in claim 18 in which said treatment is an oxidative treatment.

20. A process as claimed in claim 9 in which prior to step (a) the solution comprising rhodium and tar is submitted to a treatment whereby the rhodium present therein is converted to a more easily extractable form.

21. A process as claimed in claim 20 in which said treatment is an oxidative treatment.

22. A process as claimed in claim 1 in which said organic phase comprising methyl acetate, methyl iodide tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

23. A process as claimed in claim 22 in which said oxidant is selected from the group consisting of hydrogen peroxide, ozone and peracetic acid.

24. A process as claimed in claim 4 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

25. A process as claimed in claim 8 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

26. A process as claimed in claim 9 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

27. A process as claimed in claim 10 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

28. A process as claimed in claim 16 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

29. A process as claimed in claim 18 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

30. A process as claimed in claim 20 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

31. A process as claimed in claim 21 in which said organic phase comprising methyl acetate, methyl iodide, tar and any remaining rhodium is subjected to the further steps of (c) treatment with a carbonylation process compatible oxidant, (d) submitting the product of step (c) to an extraction with water, and (e) recovering an aqueous phase containing rhodium and an organic phase comprising tar and methyl iodide.

32. A process for the recovery of rhodium from a solution comprising rhodium and tar from a process in which acetic anhydride and/or acetic acid is produced by carbonylating methanol, methyl acetate, dimethyl ether and/or reactive derivatives thereof which process comprises the steps of:
(1) submitting said solution to an oxidative treatment whereby the rhodium present therein is converted to a more easily extractable form,
(2) submitting said treated solution from step (1) to a liquid extraction with a combination of water, methyl iodide and methyl acetate in which combination:
(i) methyl iodide is from 20 to 80% by mass of the methyl iodide plus methyl acetate, and
(ii) water is in a ratio of (0.2 to 5):1 by mass relative to the methyl acetate/methyl iodide combination, and in the liquid extraction said combination of water, methyl iodide and methyl acetate is added to said rhodium solution in the mass ratio (0.2 to 5):1.
(3) separating an aqueous phase containing rhodium from an organic phase comprising methyl acetate, methyl iodide, tar and any remaining rhodium,
(4) treating said organic phase from step (3) with a carbonylation process compatible oxidant,
(5) submitting the product of step (4) to an extraction with water, and
(6) recovering an aqueous phase containing rhodium and an organic phase comprising tar and methyl iodide.

33. A process as claimed in claim 1 in which the solution comprising rhodium and tar is obtained from an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a rhodium catalyst system, methyl iodide co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in an amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm, (v) sufficient iodide salt to provide from 0.5 to 20% by weight iodine as $I^-$ and (vi) acetic acid comprising the remainder of the composition.

34. A process as claimed in claim 12, wherein the oxygen-containing gas is air.

35. A process as claimed in claim 4 in which the solution comprising rhodium and tar is obtained from an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a rhodium catalyst system, methyl iodide co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in an amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm, (v) sufficient iodide salt to provide from 0.5 to 20% by weight iodine as $I^-$ and (vi) acetic acid comprising the remainder of the composition.

36. A process as claimed in claim 10 in which the solution comprising rhodium and tar is obtained from an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a rhodium catalyst system, methyl iodide co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm, (v) sufficient iodide salt to provide from 0.5 to 20% by weight iodine as $I^-$ and (vi) acetic acid comprising the remainder of the composition.

37. A process as claimed in claim 11 in which the solution comprising rhodium and tar is obtained from an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a rhodium catalyst system, methyl iodide co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm, (v) sufficient iodide salt to provide from 0.5 to 20% by weight iodine as $I^-$ and (vi) acetic acid comprising the remainder of the composition.

38. A process as claimed in claim 32 in which the solution comprising rhodium and tar is obtained from an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a rhodium catalyst system, methyl iodide co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in amount from 1 to 35% w/w, (ii) acetic anhydride in an amount up to 8% w/w, (iii) methyl iodide in an amount from 3 to 20% w/w, (iv) rhodium catalyst in an amount from 1 to 2000 ppm, (v) sufficient iodide salt to provide from 0.5 to 20% by weight iodine as $I^-$ and (vi) acetic acid comprising the remainder of the composition.

\* \* \* \* \*